(12) United States Patent
Zhao et al.

(10) Patent No.: US 6,436,402 B1
(45) Date of Patent: Aug. 20, 2002

(54) PROCESS FOR MAKING HUMAN PAPILLOMAVIRUS VIRUS-LIKE PARTICLES WITH IMPROVED PROPERTIES

(75) Inventors: Qinjian Zhao, Ambler; Shilu Wu, Collegeville; Walter Manger; Shishir Gadam, both of Harleysville, all of PA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 09/684,233

(22) Filed: Oct. 6, 2000

Related U.S. Application Data

(60) Provisional application No. 60/159,812, filed on Oct. 15, 1999.

(51) Int. Cl.[7] .......................... A61K 39/12; C12Q 1/70; C12Q 7/06; C12Q 7/02; C07K 1/14
(52) U.S. Cl. ...................... 424/189.1; 435/5; 435/238; 435/239; 530/350; 530/403; 530/412
(58) Field of Search ................................ 530/305, 369, 530/350, 403, 412; 435/5, 71.1, 235.1; 424/124, 304.1, 199.1, 238, 239; 436/120

(56) References Cited

U.S. PATENT DOCUMENTS

| 5,871,998 A | 2/1999 | Lowy et al. |
| 5,888,516 A | 3/1999 | Jansen et al. |
| 5,922,588 A | 7/1999 | Ludmerer |

FOREIGN PATENT DOCUMENTS

| EP | 0 864 649 A2 | | 9/1998 |
| WO | WO-99/13056 | * | 3/1999 |
| WO | WO 00/37104 | | 6/2000 |

OTHER PUBLICATIONS

McCarthy et al. Jan. 1998. Quantitative disassembly and reassembly of human papillomavirus type 11 viruslike particles in vitro. Journal of Virology, vol. 72, No. 1, pp. 32–41.*
Rose et al. 1993. Expression of human papillomavirus type 11 prorein in insect cells: in vivo and in vitro assembly of virus–like particles. Journal of virology. vol. 67. No. 4, pp. 1936–1944.*
Moroder, L. et al. "Oxidative Folding of Cystine–Rich Peptides vs Regioselective Cysteine Pairing Strategies" Biopolymers (Peptide Science) vol. 40, 207–234 (1996) pp. 207–234.
Chang, J. "A Two–Stage Mechanism for the Reductive Unfolding of Disulfide–containing Proteins" Journal of Biological Chem vol. 272, No. 1, Jan. 1997, pp. 69–75.
Ruoppol, M. et al. "Effect of Glutaredoxin and Protein Disulfide Isomerase on the Glutathione–Dependent Folding of Ribonuclease A" Biochem vol. 376, 1997, pp. 12259–12267.
Lee, Y.S., et al. "Immunological properties of recombinant hepatitits B surface antigen expressed in mammalian cell" Archives of Pharmacal Research Oct. 1998; 21 (5) 543–548.
Wampler, D.E. et al., "Multiple chemical forms of hepatitis B surface antigen produced in yeast" Proc Natl Acad Sci USA, vol. 82, Oct. 1985, pp. 6830–6834.

* cited by examiner

*Primary Examiner*—James Housel
*Assistant Examiner*—Shanon A. Foley
(74) *Attorney, Agent, or Firm*—Alysia A. Finnegan; Joanne M. Giesser

(57) ABSTRACT

Human papillomavirus virus-like particles (VLPs) are subjected to various maturation conditions, including incubation at higher temperatures, exposure to soluble metals or thios-oxidation. The resultant matured VLPs are more stable, and can be used to make a vaccine formulation with increased shelf life and higher potency.

10 Claims, 13 Drawing Sheets

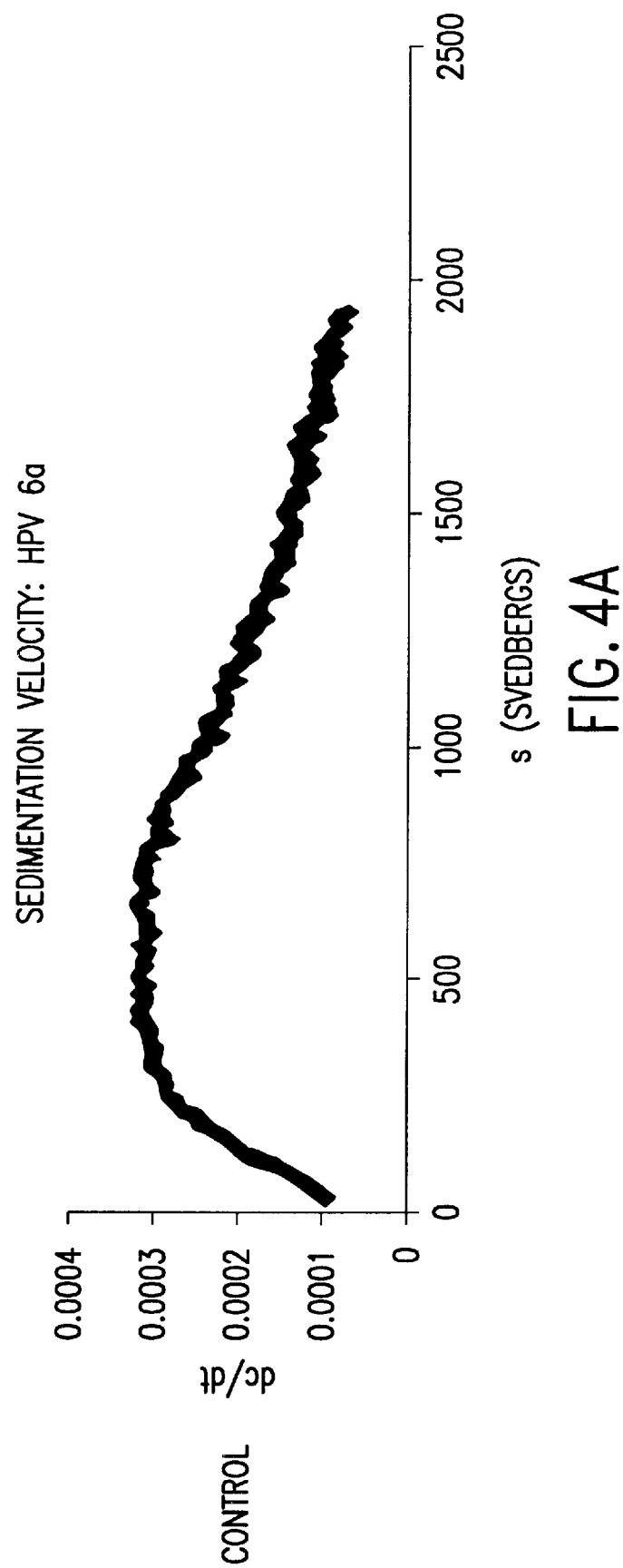

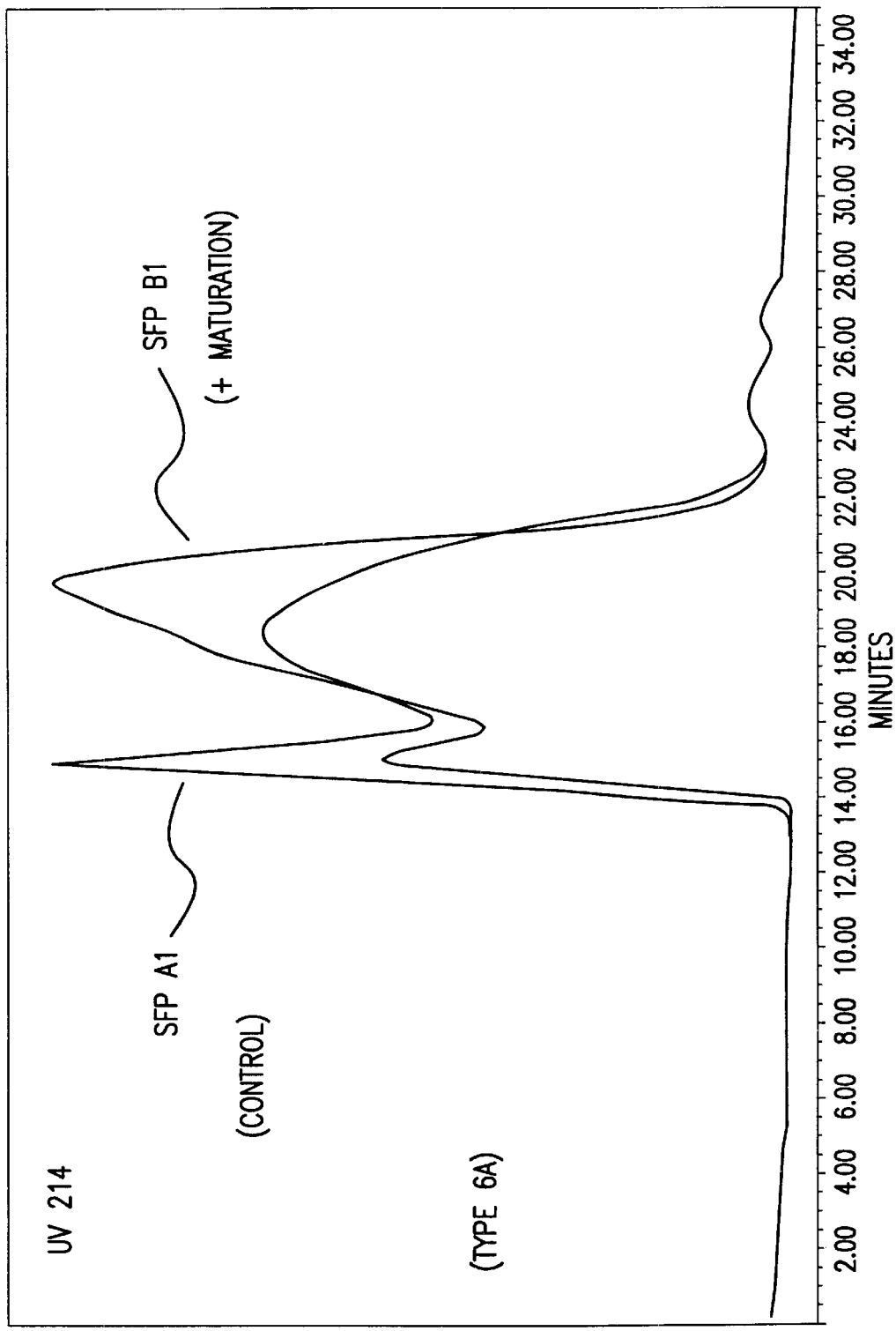

PROCESS FOR MAKING HUMAN PAPILLOMAVIRUS VIRUS-LIKE PARTICLES WITH IMPROVED PROPERTIES

This application claims benefit to U.S. No. 60/159,812 filed Oct. 15, 1999,

FIELD OF THE INVENTION

This invention relates to a novel process for purifying and processing recombinant human papillomavirus virus-like particles (VLPs), which results in compositions suitable for vaccine use which have greater stability. Also, this invention relates to the VLPs made by this process.

BACKGROUND OF THE INVENTION

Recombinant human papillomavirus (HPV) virus-like particles (VLPs), contain either L1 or a combination of L1 and L2 protein, but do not contain viral nucleic acids. They can be expressed in a variety of host cell types including yeast and insect cells and are attractive candidates for vaccine development to prevent genital HPV infection and the subsequent development of genital warts and/or cervical cancer. In animal studies, purified VLPs have been shown to induce high titers of antibodies against conformational type specific L1 epitopes. These antibodies neutralize homologous virions in in-vitro assays and protect against experimental challenge in several animal models.

"Maturation", i.e., a change in stability, structural definition and other properties of VLPs have been observed with VLPs during purification, processing and storage. While not wishing to be bound by theory, it appears that this is due, at least in part to changes in intermolecular disulfide bond formation which is required for the assembly and further stabilization of virions.

It is important for a vaccine formulation to be stable. Thus, it would therefore be desirable to make stable VLPs which also maintain immunogenicity during storage.

DETAILED DESCRIPTION OF THE INVENTION

It has been found, in accordance with this invention, that by subjecting papillomavirus L1 or L1+L2 protein to a maturation process, virus-like particles are produced which have improved antigenicity, size distribution, and stability. Thus this invention relates to a method for making human papilloma virus (HPV) virus-like particles (VLPs) comprising the steps of:
  a) expressing HPV L1 or L1+L2 proteins;
  b) at least partially purifying the proteins; and
  c) subjecting the at least partially purified proteins to a maturation step.

There are various maturations processes encompassed by this invention, including incubation at an elevated temperature, glutathione facilitated thiol oxidation, exposure to a metal surface and exposure to light. One preferred maturation process is the step of incubating the at least partially purified proteins at an elevated temperature. Thus, a specific embodiment of this invention is a method for making HPV VLPs comprising the steps of:
  a) expressing HPV L1 or L1+L2 proteins;
  b) at least partially purifying the proteins; and
  c) incubating the at least partially purified proteins at an elevated temperature.

In preferred embodiments of this invention, the proteins are recombinantly produced. Further, in other preferred embodiments, the elevated temperature is from about 30° C. to about 45° C. In a particularly preferred embodiment, the temperature is about 37° C.

In another embodiment, the at least partially purified VLPs are treated with either glutathione or oxidized glutathion as a maturation step. The resulting matured VLPs are essentially the same as the heat-treated ones.

As the VLPs produced by this method can be differentiated from those produced without the maturation step, this invention also is directed to virus-like particles (VLPs) made by the process of expressing an L1 or L1+L2 proteins, at least partially purifying the proteins, and subjecting the at least partially purified proteins to a maturation step. This invention is also directed to vaccine compositions which contain the VLPs so produced.

Another aspect of this invention is a method of inducing an immune response in an individual comprising administering to the individual an effective amount of the vaccine composition comprising VLPs which were subjected to a maturation step.

BRIEF DESCRIPTION OF THE FIGURES

FIG. 2A are VLPs made using the control process. FIG. 2B are VLPs made using the maturation process, which are significantly more uniformly-distributed than control.

FIGS. 4A and 4B are graphs showing HPV6a VLP sedimentation velocity changes. FIG. 4A is the control process. In FIG. 4B (the maturation process) a decrease in the heterogenicity of size of particles is demonstrated by analytical centrifugation.

FIGS. 5A and 5B are the results of high performance size exclusion chromatography (HPSEC) of VLPs. A larger population of VLPs is in mono-dispersed state in comparison to the corresponding control process. FIG. 5A is HPV6a VLPs; FIG. 5B is HPV11 VLPs.

Figure 1:
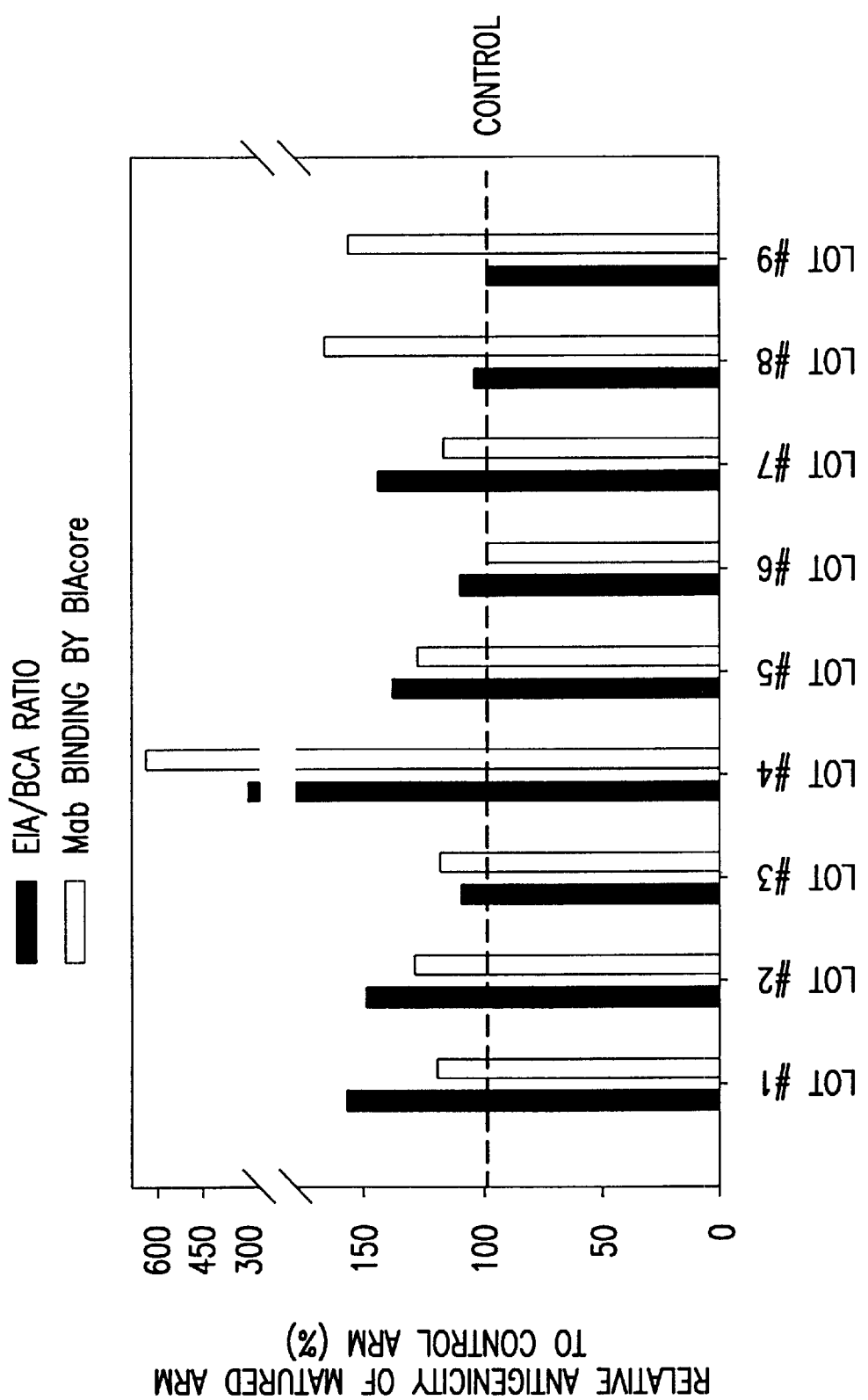
FIG. 1 is a graph showing the antigenicity enhancement obtained by including a matuation step, as determined by BIACORE analysis. EIA/BCA ratios and relative binding to neutralizing mAbs showed similar increase for the antigenicty enhancement as a result of VLP maturation. The numbers are the percent of relative antigenicity for the matured arm in comparison to corresponding controls in the same experiment. *Control arm from lot #4 showed significant aggregation in comparison to matured arm, i.e., EIA/BCA (0.3 vs 0.9) and Biacore (10 vs. 67).

As used throughout the specification and claims, the following definitions apply:

"Maturation" refers to a process rendering some beneficial changes in the properties of VLPs. VLPs which have undergone a maturation step are not sensitive to ionic strength of a solution, are stable over a broad pH range and have a half-life at room temperature, physiological salt and pH conditions of at least ½ to 2 days. In contrast, VLPs which have not been matured are highly sensitive to the ionic strength of a solution, are stable only through a narrow pH range and aggregate immediately at room temperature, physiological salt and pH.

VLPs can be assembled from naturally expressed or recombinantly produced L1 protein, which is the major capsid component of the virion of HPV. VLPs may also be made from both L1 and L2 protein, which is hereinafter designated "L1+L2".

Disulfide bonds, including inter-capsomeric disulfide bonds in particular, have been demonstrated to be critical for VLP stability and possibly VLP assembly.

General processes for making and purifying recombinant HPV VLPs are known. Virtually any serotype HPV can be used in this process. As the VLPs are ultimately to be used to make a vaccine formulation, it is preferred that serotypes associated with diseases be the ones used. These serotypes include HPV6a, HPV6b, HPV11, HPV16, HPV18, HPV31, HPV33, HPV35, HPV39, HPV45, HPV51, HPV52, HPV56, HPV58, and HPV68. The vaccine formulation may also include mixtures of VLPs from different serotypes to form a "cocktail", if desired. For example, a preferred vaccine formulation will include HPV6a and/or HPV6b, along with HPV11, HPV16, and HPV18.

The recombinant protein may be produced in any desirable host cell. Examples of known useful host cells include yeast and insect cells, although others may be used. In preferred embodiments, yeast cells, especially *Saccharomyces cereviscae* are the host. The host cells are transformed with the appropriate genetic constructs, and HPV proteins are produced, all using known methods. When sufficient L1 or L1+L2 protein is produced, the proteins are harvested and purified. In general any purification procedure may be used in accordance with this invention, so long as it contains at least one maturation step. In a generally used process, the cells may be frozen and stored as a cell slurry prior to the purification procedure.

Cells are then thawed, and if desired, the cell slurry may be diluted with a buffer. Temperatures used at this stage are typically about 5–20° C. If desired, enzymes such as BENZONASE® may be added to degrade unwanted nucleic acids. VLPs can be separated from the cell debris using a variety of techniques, including chromatography steps.

In one embodiment of this invention, the VLPs are separated using an ion exchange chromatography step, such as cation exchange chromatography. The intermediate product resulting from this process, referred to as "CEP", can either be subjected to further purification steps and a maturation step, or may be subjected to a maturation step and then further purification steps. It is generally preferred that the CEP be subjected to a maturation step.

In accordance with this invention, numerous maturation processes have been identified. Maturation results in VLPs which have increased stability as compared to capsids which have not undergone a maturation process. Maturation may be achieved by incubation at an elevated temperature, glutathione-facilitated thoil oxidation, exposure to a metal surface, or exposure to light.

In one preferred embodiment, the maturation step is an incubation at an elevated temperature. This may be performed on the CEP or on the product of a later purification step. It is typically an incubation for about 10–48 hours, preferably about 15–20 hours, at an elevated temperature. Typically elevated temperatures are from about 25° C. to about 45° C., and preferably about 37° C.

Alternatively, the CEP or a more purified product may be treated with either glutathione or oxidized glutatione in order to mature them. The absolute amount of glutathione does not appear to be critical. It may range from 0.5 mM to about 10 mM, and amounts above 1 mM are preferred. There seems to be little difference between the maturation processes using 1 mM and those using 7 mM. If oxidized glutathione is used, the amounts may range from about 0.5 mM to about 20 mM, with 1 mM to 17 mM being preferred.

The CEP or a more purified product mal be matured by exposure to a metal surface. This involves a reaction which occurs in the presence of a soluble transition metal, such as $Fe^{2+}$, $Fe^{3+}$, $CU^{1+}$ or $Cu^{2+}$. Only a catalytic amount of metal is required for the maturation reaction.

The matured product may be subjected to any other desired purification steps. In a preferred process, the matured product will be processed through a hydroxyapatite chromatography column, and then subjected to ultrafiltration to produce a final VLP product. The final product can then be formulated into a vaccine composition using known methodologies and additives, if desired.

Alternatively, the CEP can be further processed and/or purified, such as by a hydroxyapatite column chromatography process and ultrafiltration, and then matured.

The vaccine formulation of this invention comprises VLPs which are matured, along with other physiologically acceptable ingredients. For example, it may contain alum, non-ionic surfactants (such as polysorbate derivatives, and preferably polysorbate 80 or polysorbate 20), salts, and buffers. In preferred embodiments, the vaccine comprises matured VLPs, which are adsorbed to alum (200–550 µg/ml alum), 0.005–0.5% (wt/v) polysorbate or derivative, 2–10 mM buffer and either 0.10–0.20 M NaCl or, for a lower saline formulation, 0.01–0.05 M NaCl. A preferred embodiment comprises about 450 µg/ml alum, 0.03% wt/v polysorbate 80 or polysorbate 20, 5 mM histidine buffer, and either 0.15M NaCl or 0.3M NaCl.

The final formulation generally has 10–200 µg/ml VLPs, preferably either about 20 µg/ml, 40 µg/ml or 100 µg/ml VLPs. A typical dosage will be a 0.5 ml injection.

As a result of the maturation process, improvements to the VLPs result. These improved VLPs made by a maturation process are another aspect of this invention. Improvements may be classified as follows:

Enhanced Antigenicity of HPV VLPs due to Maturation. The EIA/BCA ratios for the CEPs derived from the maturation process and their respective control process for 8 lab scale process lots for type 6a and 1 lot for type 11 are detailed in Example 4. EIA/BCA ratios were found to increase approximately 30–50% when the maturation step was included. A consistent 20–30% increase in antigenicity using monoclonal antibody binding tests was observed.

FIG. 1 shows the relative antigenicity of the matured products in comparison to their respective controls (%). Relative antigenicity assay by BIAcore assay using neutralizing mAbs showed similar results for the antigenicity improvement as a result of spontaneous maturation (Example 4). The pair of CEPs from Lot #2 were formulated on Alum. IVRP assay (in vitro release potency assay,) on the Alum-adsorbed preparations also confirmed an approximate 30% enhancement in antigenicity.

Figure 3:
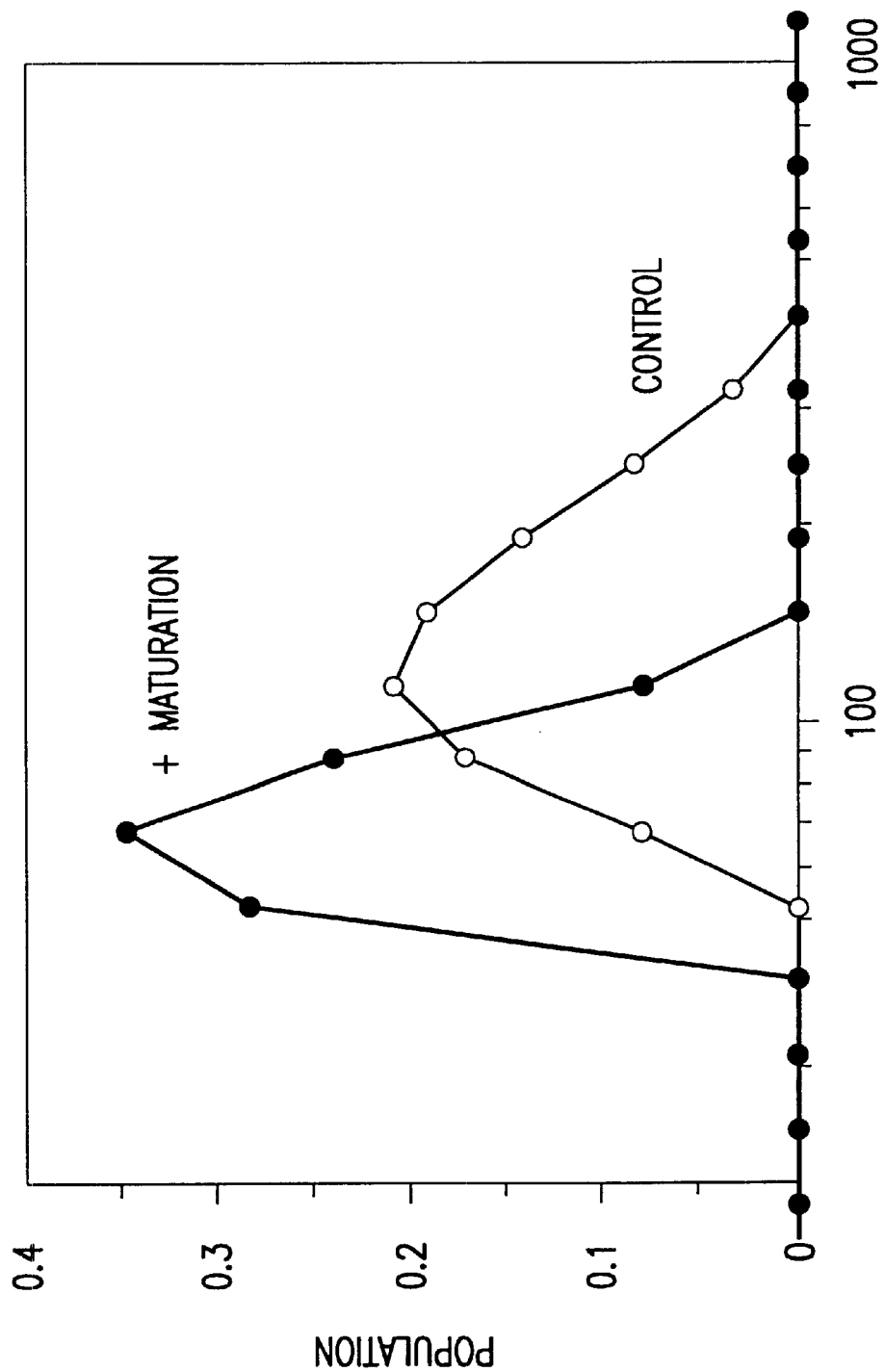
FIG. 3 is a graph showing size-distribution of VLPs analyzed by dynamic light scattering.
Figure 4B:
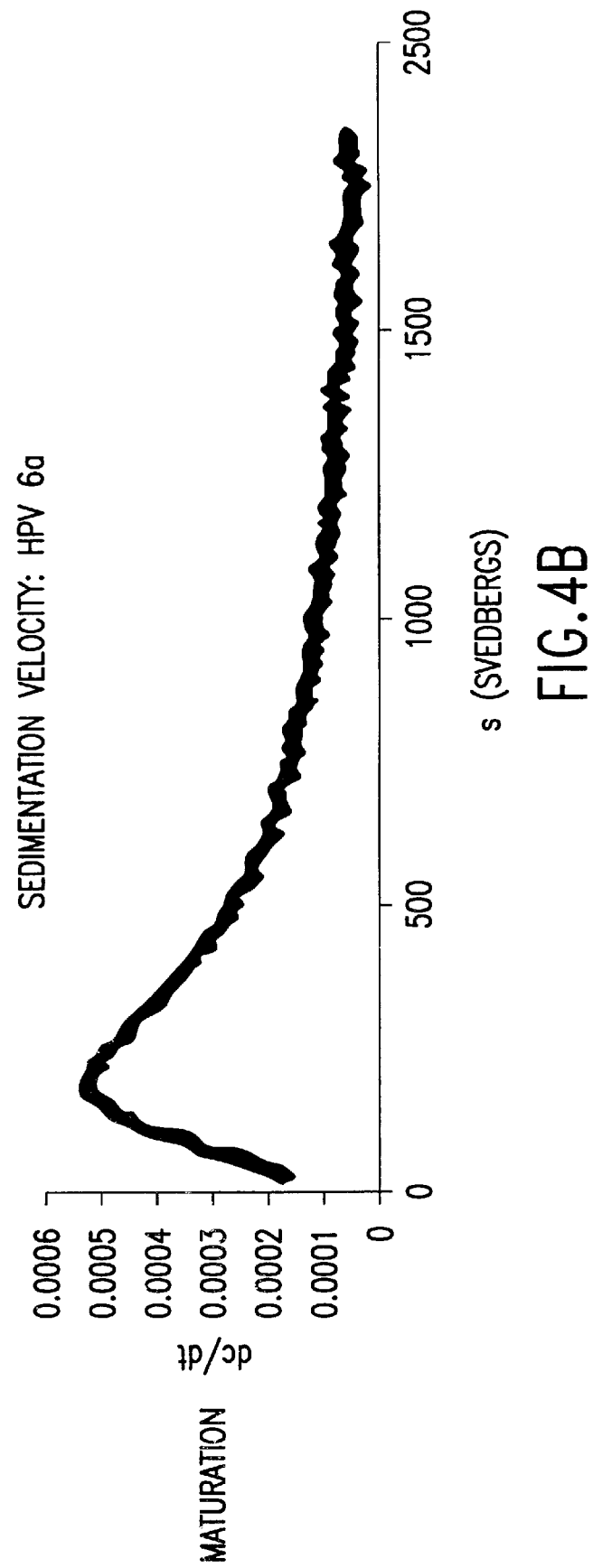
Figure 5B:
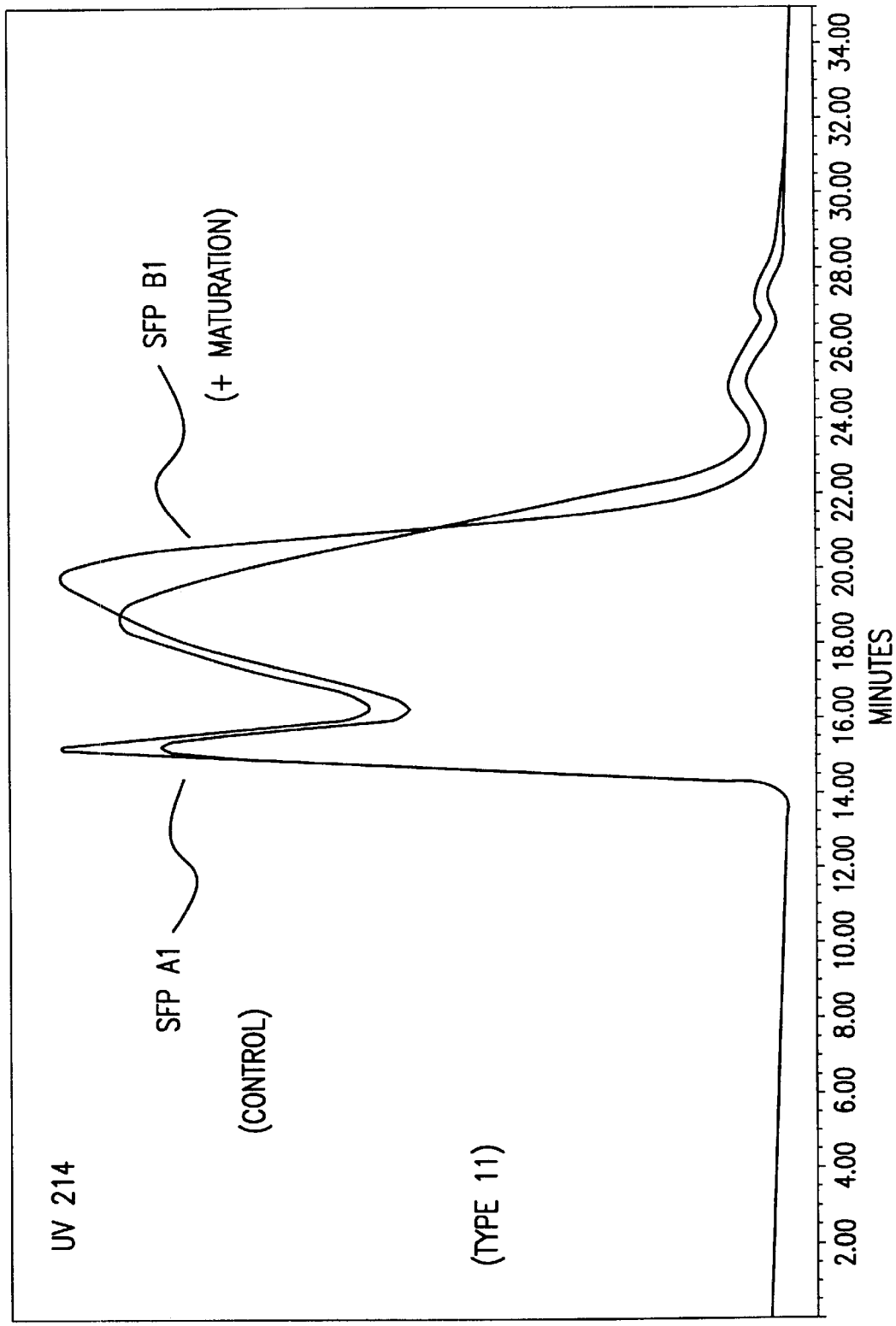
Figure 6A:
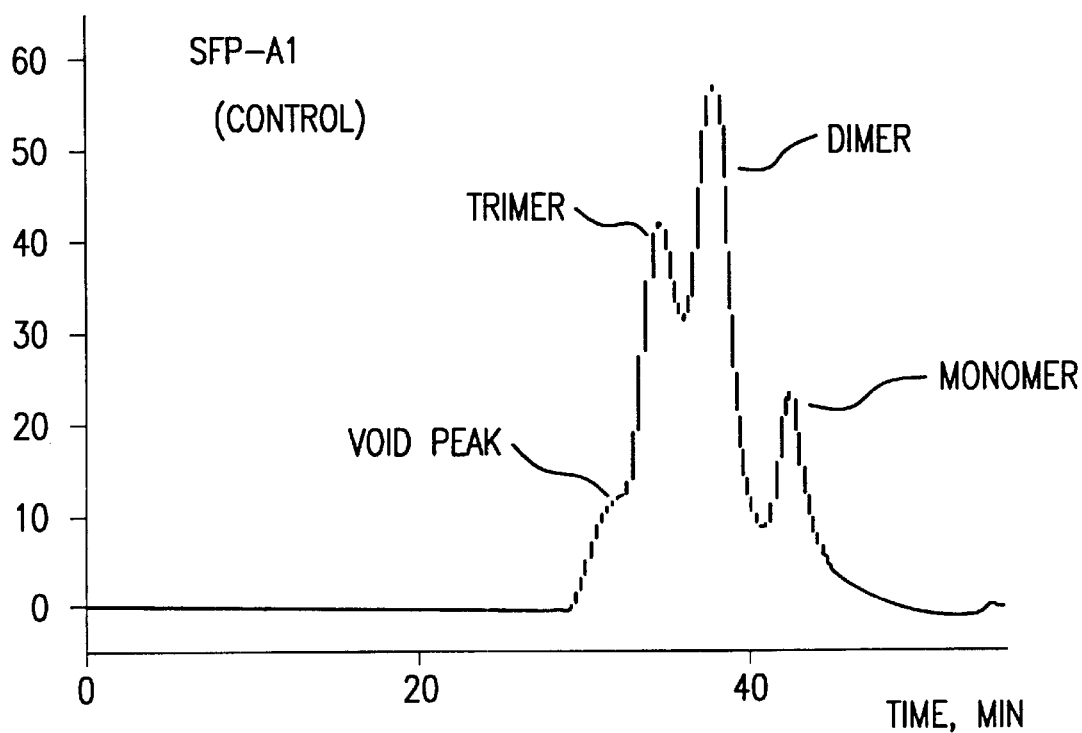
FIGS. 6A–D are graphs demonstrating more cross-linking of L1 protein as a result of maturation indicated by HPSEC under non-reducing conditions for HPV6a (FIGS. 6A and 6B) and HPV11 (FIGS. 6C and 6D). There is a significant drop in monomer content as conversion improves with maturation.
Figure 6B:
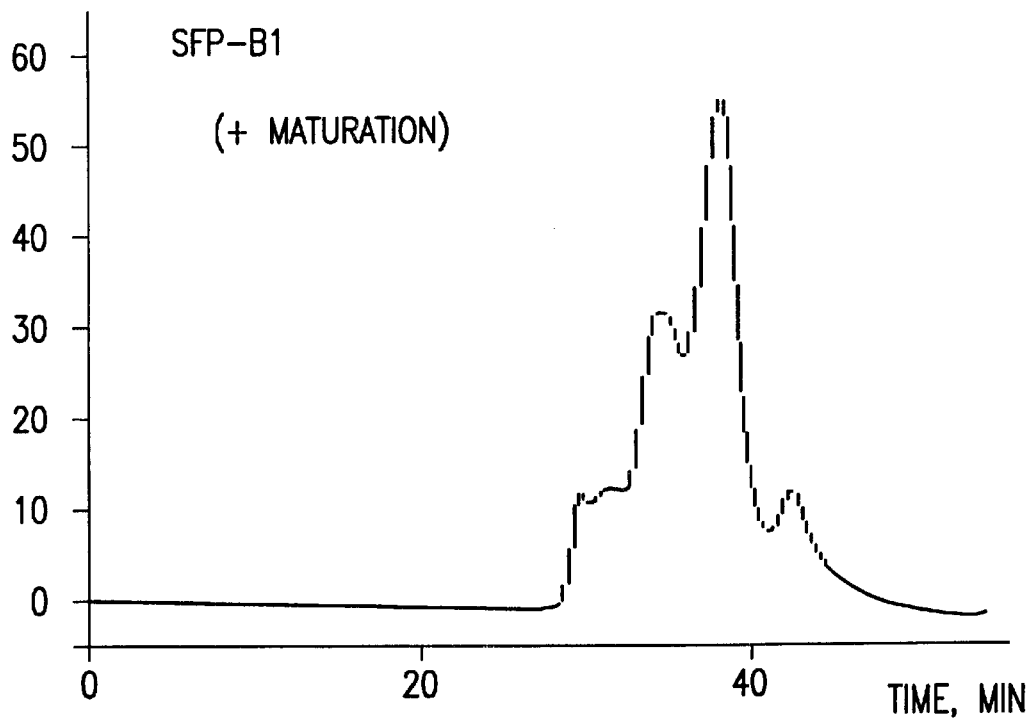
Figure 6C:
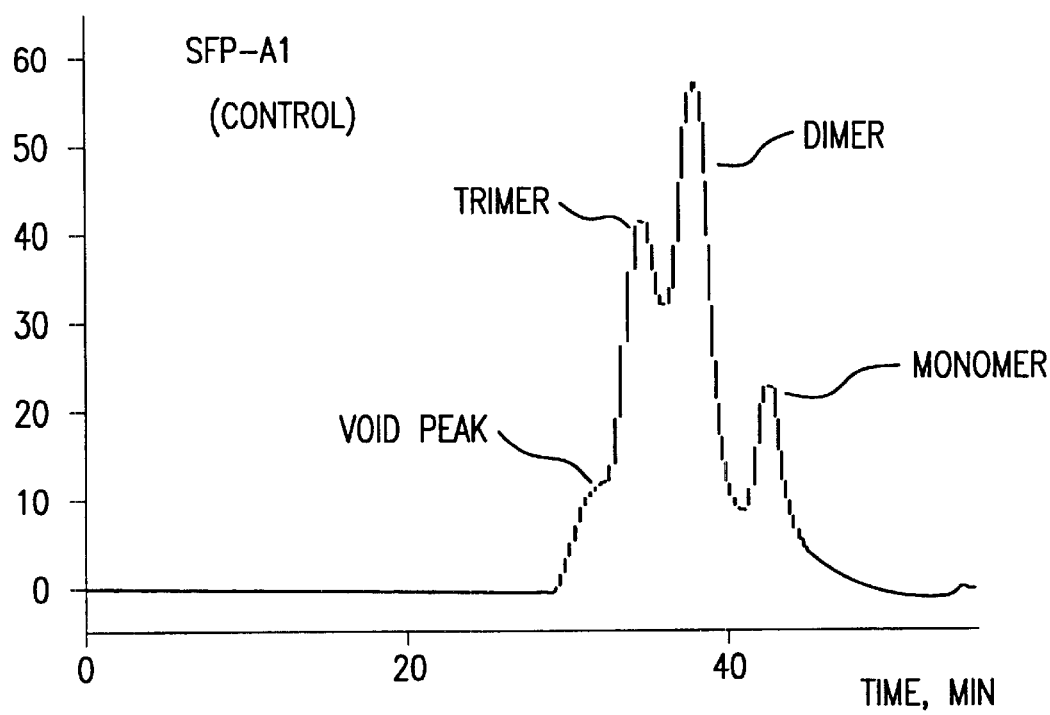
Figure 6D:
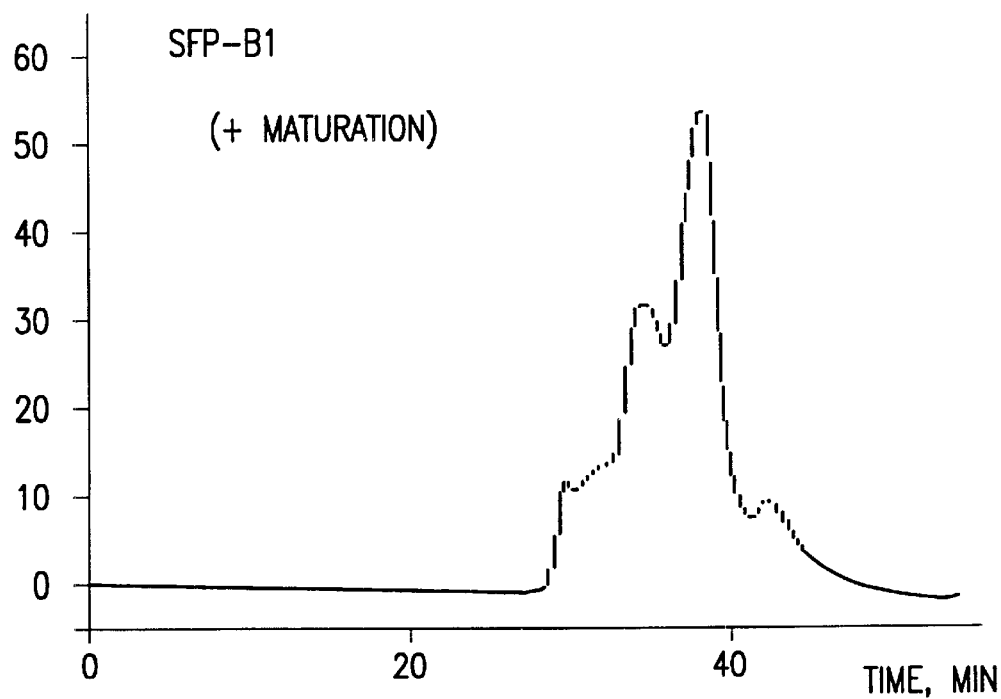

Reduction in Size and Heterogeneity of VLPs Through CEP Maturation. As VLPs mature by forming more intra- and intermolecular disulfide bonds, the VLPs become better-defined and thus less associative to one another or to container surface. The VLPs made by the maturation process consistently showed smaller in overall size. Most importantly, the heterogeneity of the VLPs was found to be reduced dramatically as indicated by EM (FIGS. 2A & 2B), size-distribution analysis by dynamic light scattering (FIG. 3) and velocity sedimentation (FIGS. 4A and 4B). Consistent with the observation made from the earlier lots, HPSEC on the recent two lots (Lot #8 and #9) showed similar results, i.e., the matured arms gave better defined and more monodisperse particles (FIGS. 5A and 5B).

Yield Enhancement upon Maturation. One of the key benefits of subjecting the CEP to a maturation step was the increased yield recovered from the hydroxyapatite chromatography (HA) step. Maturation of the VLPs results in a more selective hydroxyapatite column process, as VLPs become less associative non-specifically to one another and to solid surface. Although maturation of VLPs was tested with different starting materials for type 6a and 11, for the majority of the lots tested, the HA step yield was higher in the maturation arm compared with the control arm. For example, in one type 6a lot, the HA step yield was 33% for the maturation arm compared with 24% for the control arm. Similarly for a type 11 lot, the HA step yield was 35% for the maturation arm compared with 30% for the control.

More Cross-Linking of L1 Protein. L1 proteins have strong propensity to inter-cross-linked with the other L1 molecules from the neighboring capsomeres through disulfide bond formation. This structural consolidation process would occur regardless the temperature, conditions, or whether one would be aware about it or not, during process and during storage. Maturation of VLPs provide the conditions favorable for such conformational search and subsequent structural consolidation through inter-chain cross-linking. Tethering the capsomeres together using covalent disulfide bonds completes the assembly process for VLPs. By incorporating an incubation step, much less L1 proteins were left in the monomer stage, indicating more cross-linking within VLPs (FIGS. 6A–D).

Figure 7:
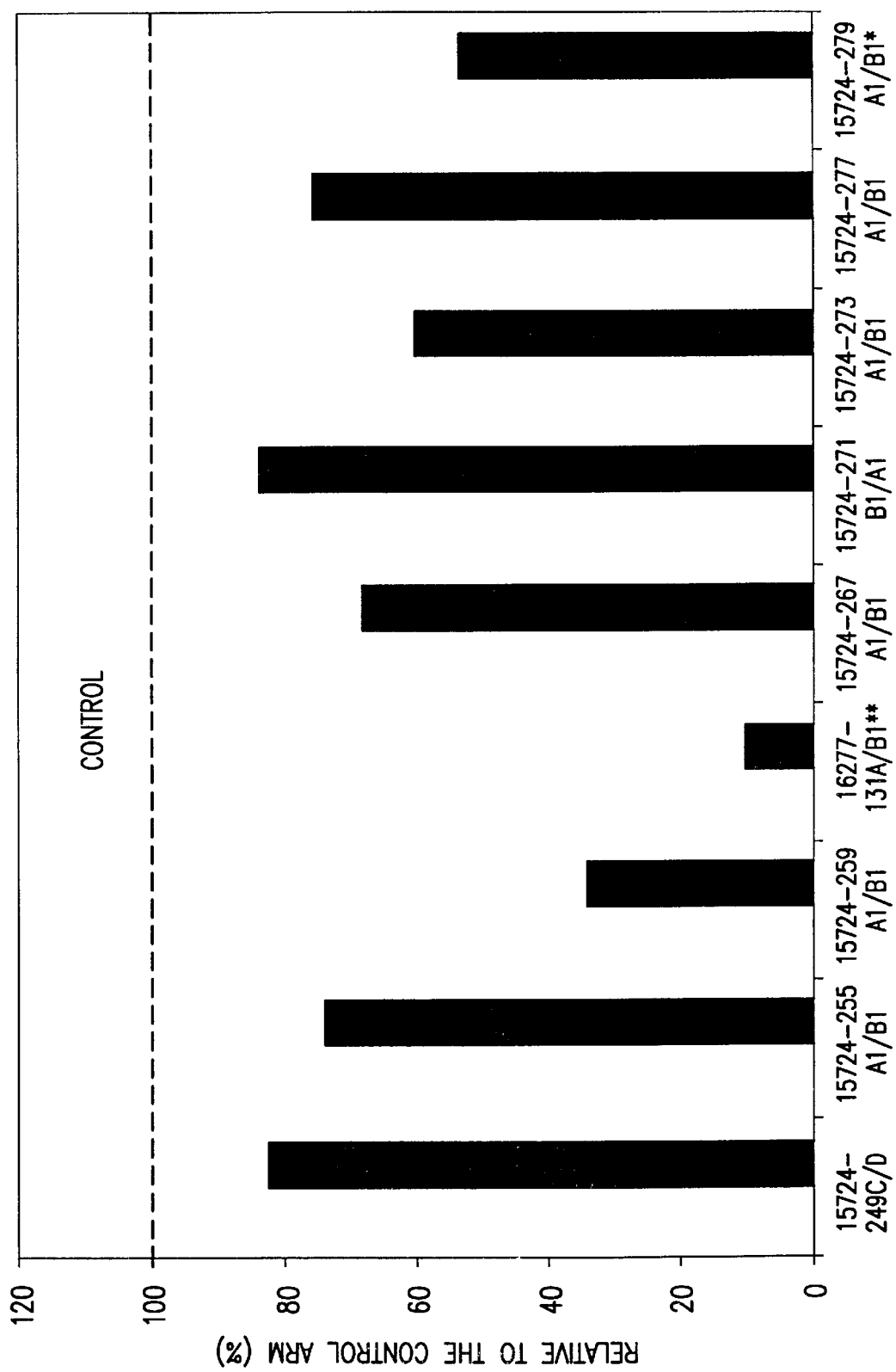
FIG. 7 is a graph showing decrease in proteolytic activity of VLPs as a result of HSP maturation during the process. All the proteolytic activities of matured VLPs were normalized to the respective control arms in the same experiments, and were assayed in pairs using casein as a substrate.
Figure 8:
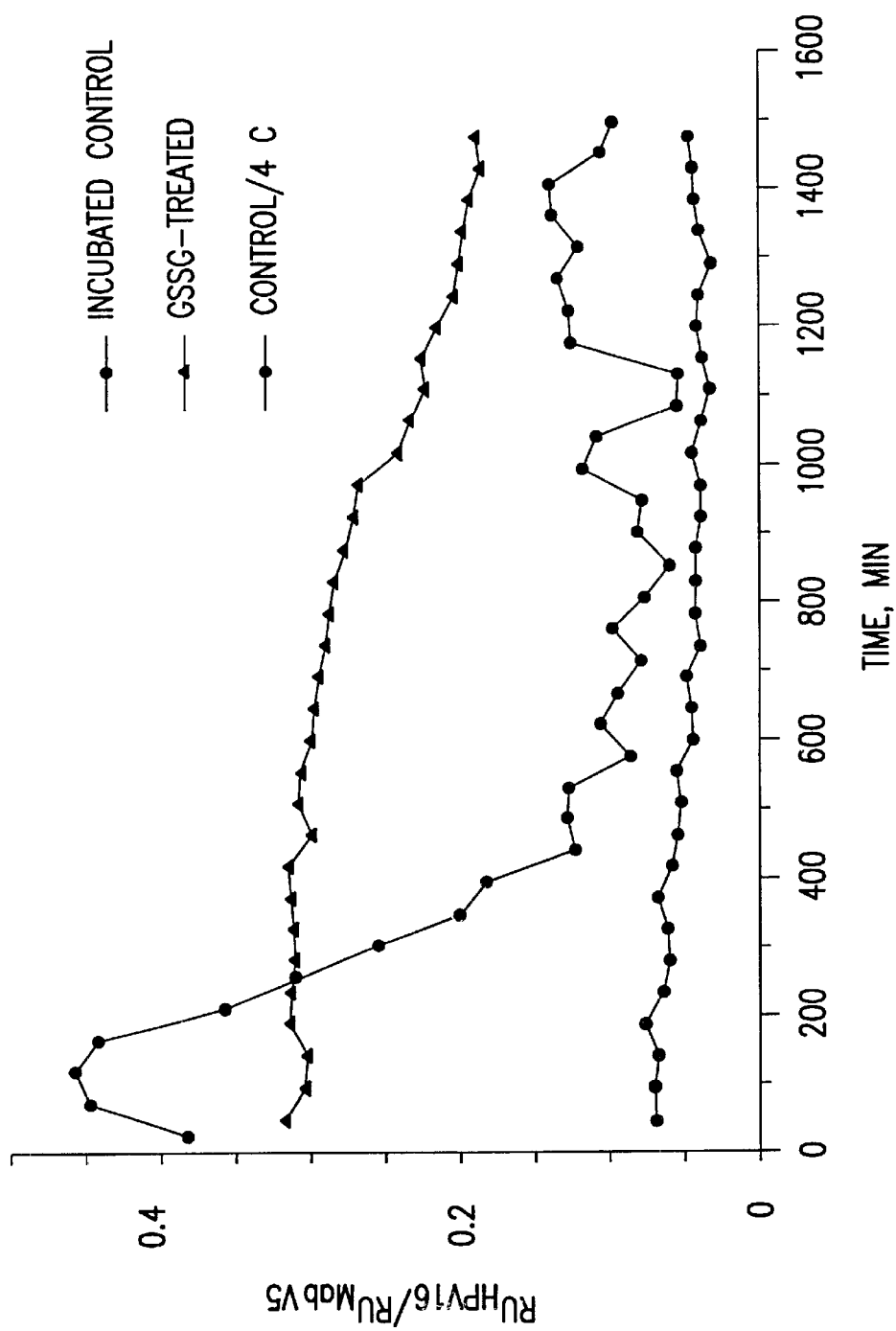
FIG. 8. Improved stability of HPV16 VLPs as a result of facilitated maturation. Control (from 4° C., filled dots) VLPs was shown to loose antigenicity quickly during 42° C. treatment, while the treated products (filled triangles) showed better stability. Another control preparation (filled dots at the bottom trace) showed that, without GSSG, HPV16 VLPs lose antigenicity during incubation.
Figure 9A:
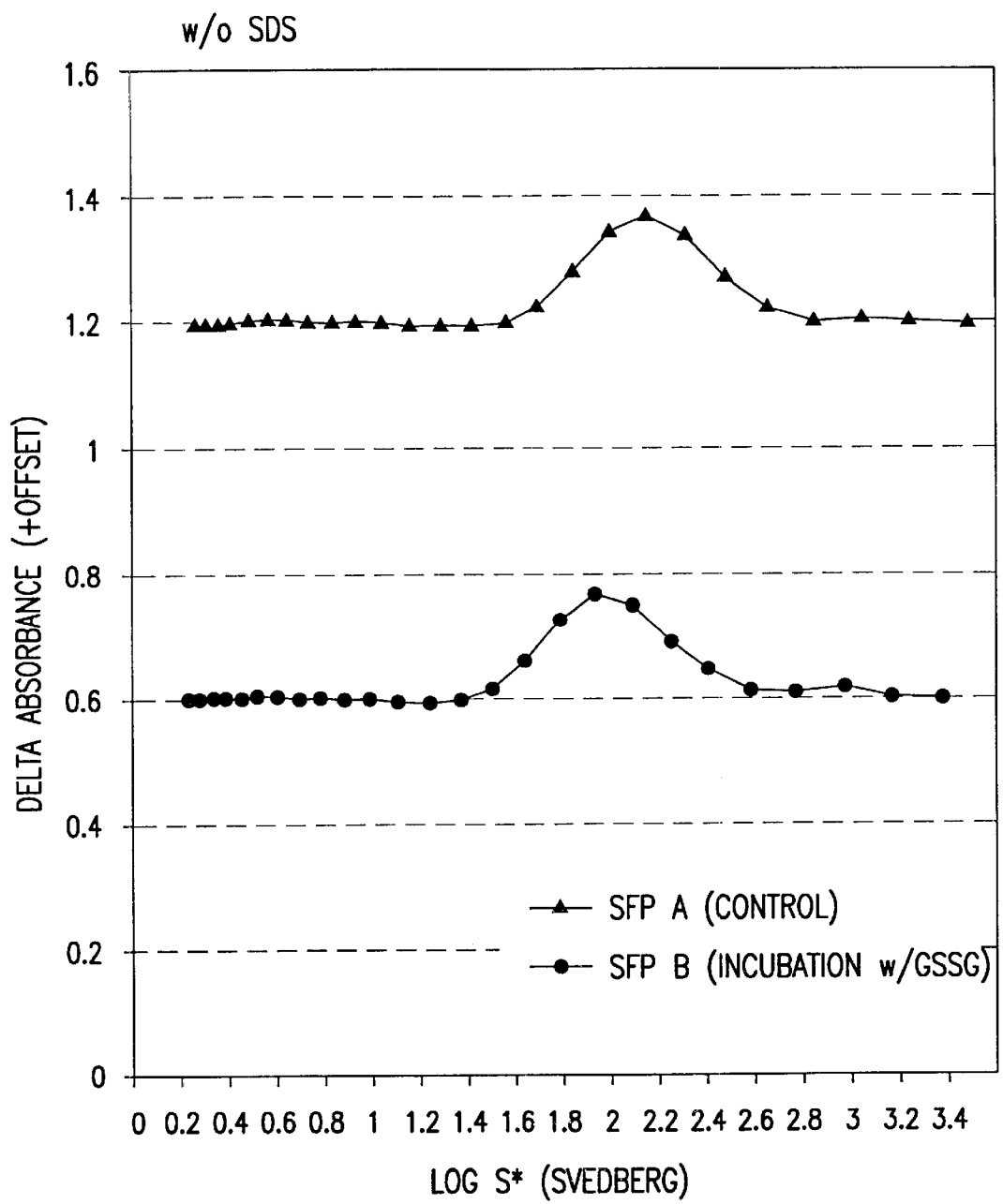
FIG. 9 Sedimentation profiles of the HPV16 VLPs of Sterile Filtered Products (SFPs) with (SFP B) or without (SFP A) redox-treatment. Left Panel: VLPs of both arms exhibit size of approximately 40–60 nm in diameters (logs* equal approximately 1.4–2.4); Right Panel: Under denaturing conditions, VLPs from control process were completely denatured to L1 protein (p55), whereas VLPs from redox-facilitated maturation retained the particulate structures.
Figure 9B:
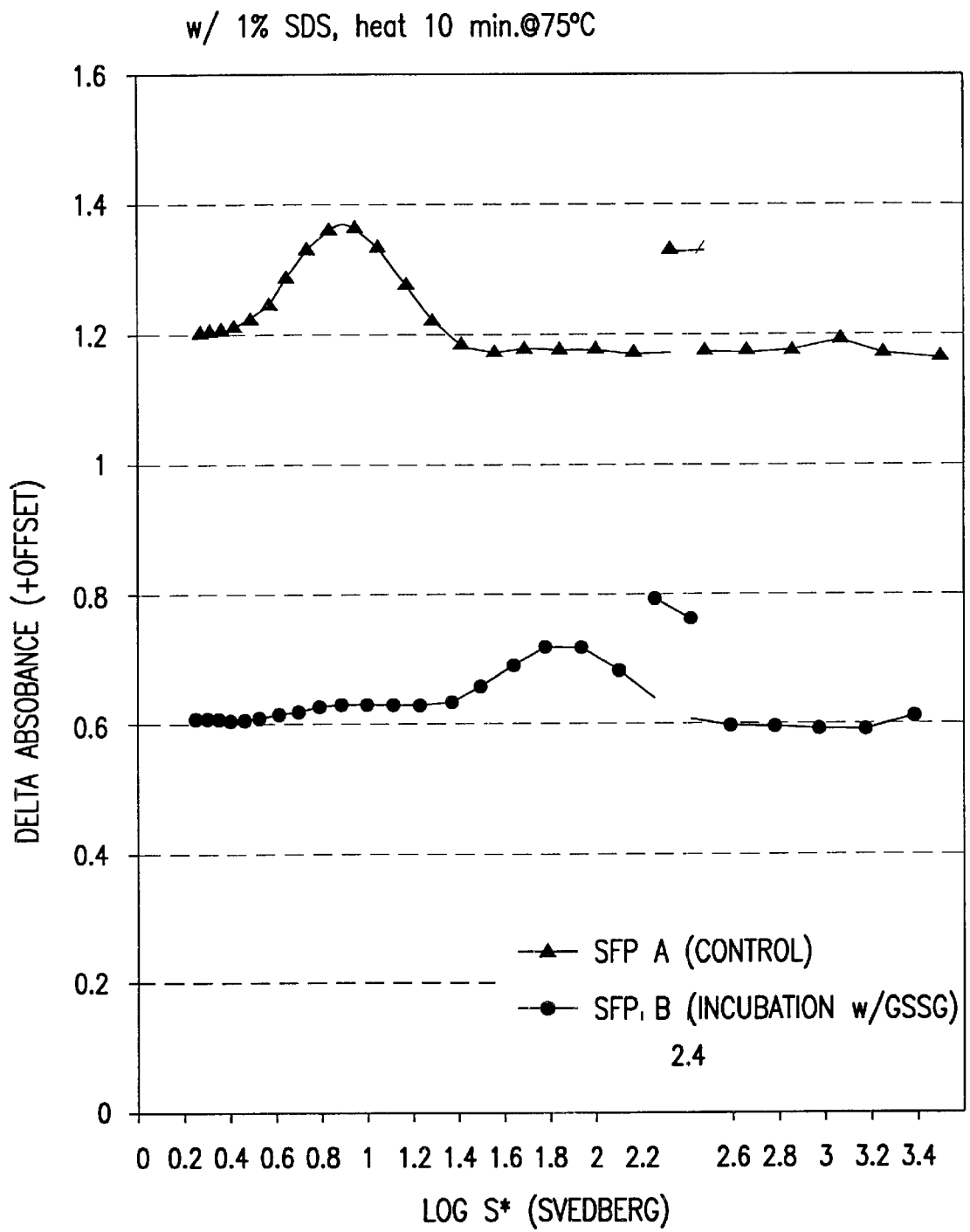

Lower Residual Proteolytic Activity Protease activity assay with a non-specific substrate indicated that overall proteolytic activity was consistently reduced for the maturation arms in comparison to their corresponding control arms (FIG. 7). While not wishing to be bound by theory, it appears that heat inactivation during incubation and better selectivity of HA column could be the mechanisms for protease inactivation and/or clearance. Experiments showed that there was slight reduction in the protease activity upon the 37° C. maturation. However, this reduction only accounted for a small portion of the total reduction in the protease activity.

Improved Antigenicity and Stability for VLPs on Alum Through Maturation. Products from one of the matured lots were formulated into Alum adsorbed products. Time "0" and 3 month stress at room temperature and 37° C. showed enhanced antigenicity as well as stability by the release IVRP assay.

The following non-limiting Examples are presented to better illustrate the invention.

EXAMPLE 1

Process Description

The yeast cells with recombinant HPV expressed were stored as 36% wet cell weight (wcw) frozen slurry stored at −70° C. The cell paste was thawed at 30° C. for two hours and diluted to about 30% slurry using the harvest buffer (200 m MOPS, 2 mM $MgCl_2$, pH 7.0). The temperature of the cell paste was maintained in the range of 5–10° C. during and after thawing. Approximately 1:1 of Benzonase® (1 µL/L) was added per gram of wcw. The 30% diluted cell slurry was passed twice through a homogenizer at 14000–15000 psig. The resultant lysate was incubated at 4° C. overnight for approximately 16 hours to reduce the size of the nucleic acids for improved clearance across the purification train. The incubated lysate was further diluted to 9% wcw by the addition of harvest buffer (200 mM MOPS, 2 mM $MgCl_2$, pH 7) and sodium citrate spike buffer (1 M sodium citrate a 200 mM MOPS, pH 7). The VLPs were separated from the cell debris using a 0.65 micron microfiltration membrane with 2.25 volumes of diafiltration against a 250 mM sodium citrate buffer using a tangential flow filtration method.

The majority of the purification was achieved with the HS POROS cation exchange chromatography step. The loaded column was washed with 8 column volumes (CV) of buffer containing 5 mM sodium phosphate, 200 mM MOPS and 800 mM NaCl. The product was eluted from the HS column with a 7 CV linear gradient between the wash buffer (800 mM NaCl) and elution buffer (1500 mM NaCl) both containing 5 mM sodium phosphate and 50 mM MOPS at pH 7.0.

Maturation at Elevated Temperature

The resulting intermediate product, designated "CEP", was allowed to incubate at 37° C. in a stainless steel or glass vessel for 17 hours. In some of the experiments the CEP was sterile filtered using a 0.22 micron Millipak unit prior to the 37° C. maturation step to minimize bioburden.

Following the maturation step, the matured CEP was processed through the Hydroxyapatite (HA) chromatography to reduce both the nucleic acid and protease levels in the HPV product. The HA column was loaded at 2 mgs of protein per ml of resin based on an on-demand BCA protein analysis. The loaded HA column was washed with 5 CV of buffer, and was eluted with a 4 CV linear phosphate gradient going from 5 mM sodium phosphate to 200 mM sodium phosphate, with both buffers containing 1.25 M NaCl at pH 7.0. An on-demand protein analysis of the HA product was carried out to determine the necessary concentration factor to be achieved during the ultrafiltration with the target protein concentration of 850 µg/ml.

Ultrafiltration was carried out using a 10 kDa hollow fiber membrane operated at 250 mg/sqft load, 6000 $s^{-1}$ shear rate, transmembrane pressure of 20 psi and Tween target of 0.03% (w/v) which allows for a calculated volume reduction during the following ultrafiltration step to target an 850 µg/ml final protein concentration. Tween-80 was added to the HA product to prevent aggregation during the UF step where the product is diafiltered against a 0.5 M NaCl solution. The resulting UF product pool was sterile filtered to produce the final aqueous product (FP). The FP was characterized using a battery of assays (see below).

As a control, the same process as above was carried out without the maturation of the CEP. Instead, the CEP was stored at 4° C. for 16 h and then processed through the HA chromatography. The overall process time for both the control and maturation process was identical (about 48 h) with the only difference being essentially the incubation temperature of the HS product (4° C. for the control process; 37° C. for the maturation process).

TABLE 1

Maturation conditions during tlie process for different process lots

| Process Lot # | Control* | Maturation at 37° C. |
|---|---|---|
| 1 (Type 6a) | | Glass, 17 hours. |
| 2 (Type 6a) | | Glass, 22 hours. |
| 3 (Type 6a) | | S. Steel, 17 hours |
| 4 (Type 6a) | 300 kd UF membrane used. | 300 kd UF membrane used. |
| 5 (Type 6a) | Used frozen 9% dilute aged lysate from Lot #3 as starting material. | S. Steel, 17 hours |
| 6 (Type 6a) | | S. Steel, 17 hours |
| 7 (Type 6a) | Used frozen HSP from Lot #6 as starting material. | S. Steel, 17 hours |
| 8 (Type 6a) | | S. Steel, 17 hours |
| 9 (Type 11) | | S. Steel, 17 hours |

*Control experiments carried out under conditions described in the Example, unless otherwise specified in the table

EXAMPLE 2

EIA Quantitation of Antigen—Antigenicity Determination

Double sandwich ELISA format was used to quantitate HPV types 6a and 11. The VLPs were captured by polyclonal goat anti-HPV6a or 11 antibodies. Conformational sensitive mouse anti-HPV mAb, B10.5 (HPV6a) and B2 (HPV11) were used to quantitate the amount of VLPs captured, coupled with a horseradish peroxidase labeled anti-mouse-IgG for detection. All experiments were carried out in 96-well plates. The peroxidase catalyzes the reaction to generate a product having OD at 450 nm which can be read by a plate reader. Reference and samples were always ran side by side. Incubation was at 37° C. for bindings of both type-specific antibodies and the conjugated antibody.

EXAMPLE 3

Biacore Assay

All Biacore assays were done with a BIACORE® 2000 or BIACORE® 3000 unit (Uppsala, Sweden) using CM5 sensorchips at 20° C. On the surface of sensorchip CM5, carboxylate groups were introduced to the dextran matrix. Rat-anti-mouse antibody or α-mouse $FC_\gamma$ were covalently immobilized to the carboxylate groups of the sensorchip surface through amine coupling. The amine coupling kit, with 0.2M N-ethyl-N'-(3-diethylaminopropyl)carbodiimide and 0.05M N-hydroxysuccinimide (NHS/EDC) for activation and ethanolamine for deactivation, was from Biacore, Inc. (Uppsala, Sweden). Neutralizing anti-HBsAg antibodies mAb B10.2 (for type HPV 6a) and B2 (for type 11), were supplied by Dr. Neil Christensen (Penn State Univ.). The mAb was captured onto the sensor surface by α-mouse $FC_\gamma$ prior to the injection of antigen or rHBsAg in aqueous solutions where the specific interactions between HPV VLPs and mAb B 10.5 or B2 were studied.

TABLE 2

Antigenicity enhancement of HPV VLPs due to CEP maturation.

| Process Lot # | EIA/BCA ratio Control | EIA/BCA ratio Maturation |
|---|---|---|
| 1 (Type 6a) | 1.2 | 1.9 |
| 2 (Type 6a) | 1.0 | 1.5 |
| 3 (Type 6a) | 1.7 | 1.9 |
| 4** (Type 6a) | 0.3 | 0.9 |
| 5 (Type 6a) | 1.5 | 2.1 |
| 6 (Type 6a) | 1.6 | 1.8 |
| 7 (Type 6a) | 1.5 | 2.2 |
| 8 (Type 6a) | 1.2 | 1.3 |
| 9 (Type 11) | 1.2 | 1.2 |

*UF was carried out with a 300 k membrane and therefore experienced significant extent of aggregation.

TABLE 3

Antigenicity enhancement of VLPs with maturation as detennined by BIAcore (mAb B1O.5 or B2 Binding)

| Lot # | Ratio (+/−M) for FPs | Control | Maturation | Reference SFP |
|---|---|---|---|---|
| 1 (Type 6a) | 1.2 | 262 | 338 | Lot #100 |
| 2 (Type 6a) | 1.3 | 116 | 172 | Lot #100 |
| 3 (Type 6a) | 1.2 | 109 | 124 | Lot #101 |
| 4* (Type 6a) | — | 10 | 67 | Lot #101 |
| 5 (Type 6a) | 1.3 | 127 | 160 | Lot #101 |
| 6 (Type 6a) | 1.0 | 146 | 149 | Lot #101 |
| 7 (Type 6a) | I.2 | 115 | 141 | Lot #101 |
| 8 (Type 6a) | 1.7 | 77 | 129 | Lot #101 |
| 9 (Type 11) | 1.6 | 78 | 127 | |

* Control arm experienced extensive aggregation due to 300 kDa UF.

EXAMPLE 4

Electron Microscopy

Electron microscopy (EM) on all of the sterile filtered products was performed by the EMBS labs in Elkridge, Md. The samples were stored from the time of generation until ready for the EM analysis at −70° C. Samples were thawed at room temperature for 45 minutes and then resuspended thoroughly by gentle tube inversion and swirling before gris preparation. Each sample submitted for the analysis was diluted in 0.5M NaCl buffer in various dilution factors in the range of 2 to 8. Each sample was re-suspended thoroughly after dilution. 300-mesh copper grids coated with formvar and carbon were clamed tightly and secured with forceps. Each grid was rinsed with 0.01% bovine serum albumin and the excess solution was then wicked off using filter paper. A 2 μl aliquot of 2% VLP sample was placed on separate grids and allowed to dry. After 10 minutes, any residual material was wicked from the grids. After each sample had completely air dried, the samples were fixed and stained with 20 μl of 2% phosphotungstic acid which was placed onto each grid and allowed to incubate for 30 seconds. Any excess stain was removed with filter paper. The samples were intensively examined in a JEOL 1200 EX Transmission Electron Microscope (TEM) at high magnifications. Numerous areas from each grid were thoroughly examined before micrographs were taken. The samples were prepared diluted 1:2 through 1:8 in order to consistently examine samples in the 100 to 150 μg/ml BCA concentration range.

Figure 2A:
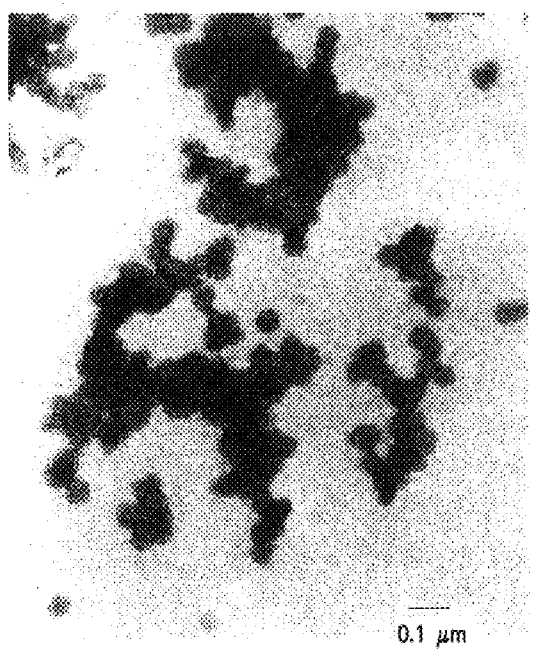
FIGS. 2A and 2B are electron micrographs of VLPs of final products.
Figure 2B:
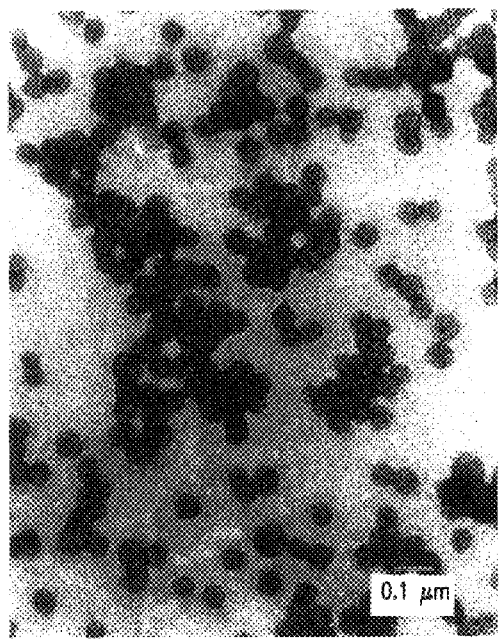

Results are shown in FIGS. 2A and 2B.

EXAMPLE 5

High Performance Size Exclusion Chromatography (HPSEC)

A Shodex SB-805-HQ column was used in the HPSEC analysis. The exclusion limit of this column exceeds $R_\eta$=65 nm (dextran standard) but is less than $R_\eta=110$ nm (polyacrylamide standard). The column was conditioned with partially aggregated HPV18 and HPV16 samples prior to use. The areas of several injections were compared to ensure proper conditioning. Several HPV and non-HPV (dextran) size/reference standards were injected first, followed by the HPV 6a and HPV 11. Each sample was injected in duplicate using a Waters 2690 pump (flow rate: 0.4 mL/min). The mobile phase was 0.75 M NaCl, buffered by 20 mM sodium phosphate, pH 7.0. The chromatography was monitored by UV ($\lambda$=214, 260, and 280 nm) and fluorescence (ex $\lambda$=280 nm, em $\lambda$=340 nm).

EXAMPLE 7

Dynamic Light Scattering (DLS)

DLS measurements were carried out using a Malvern Zetasizer 3000 instrument. All samples and diluents were brought to room temperature prior to the measurement. The monomodal analysis algorithm was employed. Five repeat measurements (each with a 10 second duration) were carried out for each sample. Samples were diluted using the appropriate matrix buffers for the sample of interest such that the background buffer composition did not alter significantly upon dilution. The dilution factor was such that the intensity of the signal was in the range of 100–500 Kpcs. Typically, the SFP samples require a dilution factor of approximately 25.

For size distribution, a dynamic light scattering machine DynaPro-LSR (Protein Solutions, Inc., Charlottesville, Va.) was used. Samples were diluted into 0.5M NaCl to final concentration of approximately 20 $\mu$g/ml prior to the assay. Results are summarized in FIG. 3.

TABLE 4

Antigenicity enhancement of purified VLPs with maturation as determined by BIAcore (mAb B1O.5 or B2 Binding)

| Lot # | Ratio (+/−M) for FPs | Control | Maturation | Reference SFP |
|---|---|---|---|---|
| 1 (Type 6a) | 1.2 | 262 | 338 | Lot #100 |
| 2 (Type 6a) | 1.3 | 116 | 172 | Lot #100 |
| 3 (Type 6a) | 1.2 | 109 | 124 | Lot #101 |
| 4* (Type 6a) | — | 10 | 67 | Lot #101 |
| 5 (Type 6a) | 1.3 | 127 | 160 | Lot #101 |
| 6 (Type 6a) | 1.0 | 146 | 149 | Lot #101 |
| 7 (Type 6a) | 1.2 | 115 | 141 | Lot #101 |
| 8 (Type 6a) | 1.7 | 77 | 129 | Lot #101 |
| 9 (Type 11) | 1.6 | 78 | 127 | |

*Control arm experienced extensive aggregation due to 300 kDa UF.

TABLE 5

Reduction in size and heterogeneity of HPV VLPs in CEP due to maturation

| Process Lot # | DLS (nm) Control | DLS (nm) + Maturation |
|---|---|---|
| 1 (Type 6a) | 120 ± 2 | 80 ± 2 |
| 2 (Type 6a) | 116 ± 3 | 104 ± 8 |
| 3 (Type 6a) | 100 ± 7 | 96 ± 2 |
| 5 (Type 6a) | 125 ± 5 | 121 ± 2 |
| 6 (Type 6a) | 136 ± 11 | 119 ± 4 |
| 7 (Type 6a) | 166 ± 4 | 102 ± 3 |
| 8 (Type 6a) | 138 ± 1 | 116 ± 1 |
| 9 (Type 11) | 128 ± 2 | 119 ± 2 |

EXAMPLE 7

Sedimentation Velocity Analytical Centrifugation

Sedimentation velocity experiments were performed using a Beckman XLI analytical ultracentrifuge. The sedimentation coefficient distribution profiles were generated using Microsoft Excel worksheet based on the variable speed sedimentation profiles as developed for use with HPV. A small volume of the sample was loaded in a glass cell and the sample was spun at very high speeds with online UV detection to characterize the sample size distribution. Results are summarized in FIGS. 4A and 4B.

EXAMPLE 8

Cross-linking of L1 Protein: Oligomer Assay by HPSEC

Trimer, dimer and monomer contents were quantitated by running the high performance size exclusion chromatography (HPSEC) under denaturing but non-reducing conditions. Disulfide bonds were known to undergo extensive reshuffling. Therefore, low pH was employed to minimized the reshuffling. Final sample conditions were 5% sodium duodecylsulfonate (SDS)/0.1% trifluroacetic acid (TFA) with a protein concentration of 200 $\mu$g/ml. Samples were vortexed for 5 s and heated at 75° C. for 10 min (±10 s). Samples sat at room temperature for no more than 5 min before injecting onto column. Chromatography was performed on a Hewlett-Packard 1100 series HPLC using a Shodex KW-803 silica gel column. The mobile phase was 0.1% SDS/15 mM NaPi/150 mM NaCl at pH 3. Mobile phase buffer was made using monobasic NaPi and the pH lowered using HCl. A 100 $\mu$l sample injection was eluted at a flow rate of 0.2 ml/min for 90 min at room temperature. The elution was monitored at 220 nm. Results are summarized in FIGS. 5A–B and 6A–D.

EXAMPLE 9

Proteolytic Activity Assay

All of the intermediate process as well as final product samples were assayed for total proteolytic activity. An EnzChek kit from Molecular Probes was modified and used to monitor the non-specific cleavage of casein leading to the release of fluoroscently-labeled peptides.

TABLE 6

Reduction in proteolytic activity of FPs due to CEP maturation.

| Process Lot # | Control | Maturation |
|---|---|---|
| 1 (Type 6a) | 139 | 114 |
| 2 (Type 6a) | 114 | 84 |
| 3 (Type 6a) | 415 | 141 |
| 4 (Type 6a)* | 120 | 12 |
| 5 (Type 6a) | 88 | 60 |
| 6 (Type 6a) | 136 | 114 |
| 7 (Type 6a) | 114 | 69 |
| 8 (Type 6a) | 108 | 82 |
| 9 (Type 11) | 170 | 91 |

*300 kd membrane used instead of 10 kd for both control and maturation arms

TABLE 7

Yield enhancement for HA chromatography as a result of maturation

| Process Lot # | HA step yields (Control) | HA step yields (Control) |
|---|---|---|
| 1 (Type 6a) | 27 | 34 |

TABLE 7-continued

| Yield enhancement for HA chromatography as a result of maturation | | |
|---|---|---|
| Process Lot # | HA step yields (Control) | HA step yields (Control) |
| 2 (Type 6a) | 21 | 27 |
| 10 | 35 | 35 |
| 5 (Type 6a) | 34 | 23 |
| 6 (Type 6a) | 20 | 29 |
| 7 (Type 6a) | 23 | 34 |
| 8 (Type 6a) | 24 | 33 |
| 9 (Type 11) | 30 | 35 |

TABLE 8

Antigenicity and stability of type 6a absorbed to Alum for the matured product and its corresponding control by in vitro relative potency assay*

| | | | + Maturation (BI) | |
|---|---|---|---|---|
| Sample ID | Control (A1) Theoretical Concentration (μg/ml) | Average Concentration (μg/ml) | Theoretical Concentration (μg/ml) | Average Concentration (μg/ml) |
| Time "0"* | 130* | 124 (124, 124, 126) | 156 | 145 (153, 143, 150) |
| 3 Mo @ RT | 130 | 88 (89, 93, 83) | 156 | 136 (125, 131, 151) |
| 3 Mo @ 37° C. | 130 | 73 (78, 72, 70) | 156 | 121 (117, 123, 123) |

*Time "0" measurements were made using normal 160 μg/ml for the dilution.

Therefore, a correction factor, 160/130 or 160/156, was used to correct the original number.

EXAMPLE 10

Stabilization of Purified HPV16 by Glutathione-Facilitated Maturation: Minimized and Slower Loss of Antigenicity as Shown by Neutralizing mAb V5 Binding The final product of purified VLPs of HPV 16 (approximately 0.8 mg/ml in 0.5 M NaCl) was treated with oxidized form of glutathione (GSSG, 1–17 mM) to facilitate the maturation or cross-linking process. The mixture was allowed to stay at 37° C. without agitation for 16–20 hrs. The antigenicity of the HPV16 VLPs was monitored by the binding of a neutralizing mAb (H16.V5) with surface plasmon resonance or BIAcore sensor-chip based-assays. The antigenicity is expressed as the ratio of antigen (HPV 16 VLPs) over antibody (mAb V5).

It is evident in FIG. 8, untreated control is unstable during heat stress at 42° C. It completely lost antigenicity in approximately 6 hrs at 42° C. (filled dots, FIG. 8). Interestingly, GSSG treated HPV16 VLPs was found to retain more than 50% antigenicity at 42° C. after 25 hrs (filled triangle, FIG. 8). These results clearly indicates that HPV 16 VLPs after facilitated maturation with glutathione treatment are much more stable and resistant to heat-induced aggregation. GSSG-promoted disulfide bond formation has been well-known in protein chemistry, which is the likely the mechanistic basis at molecular level to tighten up the intermolecular interactions. As a results, VLPs structures are better-defined and less prone to aggregation.

EXAMPLE 11

Stabilization of HPV16 VLPs by in-Process Glutathione-Facilitated Maturation of Partially Purified CEP: Resistance to SDS-Induced Denaturation as a Result of GSSG-Mediated Oxidative Refolding.

Using the same procedure described in Example 1, HPV 16 VLPs were purified and VLPs were matured as following. The partially purified CEP was treated with a redox cocktail buffer of 1 mM GSSG, 0.1 mM GSH, and 50 μM $FeCl_2$ at 25° C. for 20 hrs. Then the mixture was process as usual through HA column and subsequent ultrafiltration for buffer exchange into 0.5 M NaCl. A control arm was carried out for comparison. All the experimental conditions were the same except that no redox buffer was used. Results in FIG. 9 clearly demonstrated the improved stability of the VLPs after maturation. Under native conditions (left panel), both control and treated products showed that VLPs have the size between 40–60 nm in diameter. The effects of redox treatment becomes evident when the VLPs were subjected to denaturing conditions—1% SDS and heating. Under the same conditions, untreated control broke into denatured subunit (L1 protein), whereas the treated preparation remain as virus-like structures from the sedimentation profiles.

What is claimed is:

1. A method for making human papillomavirus (HPV) virus-like particles (VLPs) comprising the steps of:

a) expressing HPV L1 or L1+L2 proteins;

b) at least partially purifying the proteins; and c) subjecting the at least partially purified proteins to a maturation step wherein the maturation step is selected from the group consisting of:

1. glutathione facilitated thiol oxidation using 0.5 mM to about 10 mM glutathione;
2. glutathione facilitated thiol oxidation using 0.5 mM to about 25 mM oxidized glutathione; and
3.1 or 2 in combination with incubation at a temperature from about 30° C. to about 45° C. for about 10 to 48 hours and/or alternatively in combination with exposure of the at least partially purified protein to a metal surface.

2. A method according to claim 1 wherein the HPV protein is selected from the group consisting of HPV6a, HPV6b, HPV11, HPV16, HPV18, HPV31, HPV33, HPV35, HPV39, HPV45, HPV51, HPV52, HPV56, HPV58, and HPV68.

3. A method for making HPV VLPs according to claim 2 wherein the proteins are purified prior to step c).

4. A method according to claim 1 wherein step 3) comprises incubating the at least partially purified proteins at a temperature from about 30° C. to about 45° C.

5. A method according to claim 4 wherein step 3) comprises incubating the at least partially purified protein for about 15 to about 20 hours.

6. A method according to claim 1 wherein glutathione is present at 1 mM to 7 mM.

7. A method according to claim 1 wherein oxidized glutathione is present at 1 to 17 mM.

8. An HPV virus like particle (VLPs) made by the process of claim 1.

9. A vaccine composition comprising a VLP of claim 1.

10. A method of inducing an immune response in an individual comprising administering to the individual an effective amount of the vaccine composition of claim 9.

* * * * *